(12) United States Patent
Ingallina et al.

(10) Patent No.: US 6,586,360 B1
(45) Date of Patent: Jul. 1, 2003

(54) CATALYST SYSTEM FOR THE OXIDATIVE DEHYDROGENATION OF ALKYLAROMATICS OR PARAFFINS TO THE CORRESPONDING ALKENYLAROMATICS OR OLEFINS

(75) Inventors: Patrizia Ingallina, S. Donato Mil.se (IT); Luciano Carluccio, S. Donato Mil.se (IT); Giuseppe Bellussi, Piacenza (IT); Gastone Del Piero, Milan (IT); Eugenio Andreoli, Mantova (IT); Renato Paludetto, Milan (IT)

(73) Assignees: Enichem S.p.A., San Donato Milanese (IT); EniTecnologie S.p.A., San Donato Milanese (IT)

( * ) Notice: Subject to any disclaimer, the term of this patent is extended or adjusted under 35 U.S.C. 154(b) by 0 days.

(21) Appl. No.: 09/586,789

(22) Filed: Jun. 5, 2000

(30) Foreign Application Priority Data

Jun. 3, 1999 (IT) .......................... MI99A1242

(51) Int. Cl.⁷ ................................. B01J 23/22
(52) U.S. Cl. ...................................... 502/353
(58) Field of Search ................. 502/353, 340, 502/349

(56) References Cited

U.S. PATENT DOCUMENTS 3,919,120 A * 11/1975 Kato et al. ............... 252/466 B
5,188,886 A * 2/1993 Dupon et al. ............... 428/209
5,470,815 A * 11/1995 Kim et al. .................. 502/304

* cited by examiner

*Primary Examiner*—Stanley S. Silverman
*Assistant Examiner*—Edward M. Johnson
(74) *Attorney, Agent, or Firm*—Oblon, Spivak, McClelland, Maier & Neustadt, P.C.

(57) ABSTRACT

Catalytic system for the oxidative dehydrogenation of alkylaromatics (in particular ethylbenzene) or paraffins to the corresponding alkenylaromatics (in particular styrene) or to the corresponding olefins, consisting of:

a vanadium oxide;

a bismuth oxide;

and a carrier based on magnesium, wherein the vanadium, expressed as $V_2O_5$, is in a quantity ranging from 1 to 15% by weight, preferably from 2 to 10%, the bismuth, expressed as $Bi_2O_3$, ranges from 2 to 30% by weight, preferably from 5 to 25% by weight, the complement to 100 being the carrier.

9 Claims, 10 Drawing Sheets

FIG. 3.1A
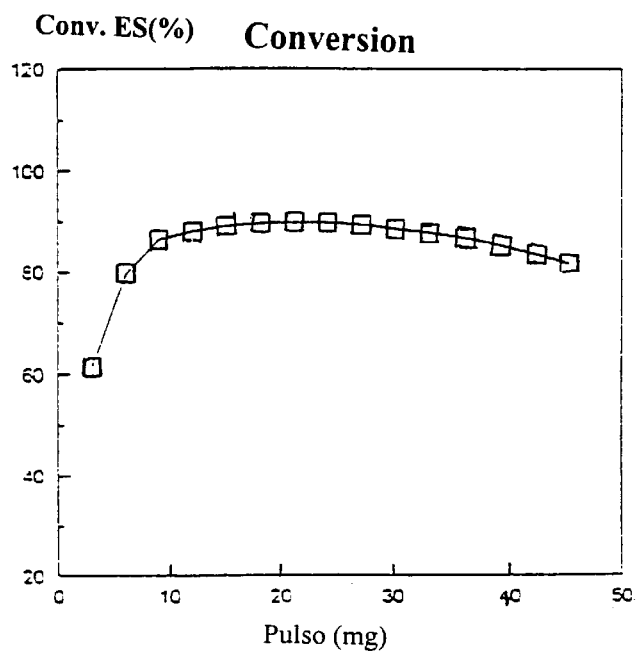
FIG. 3.1B
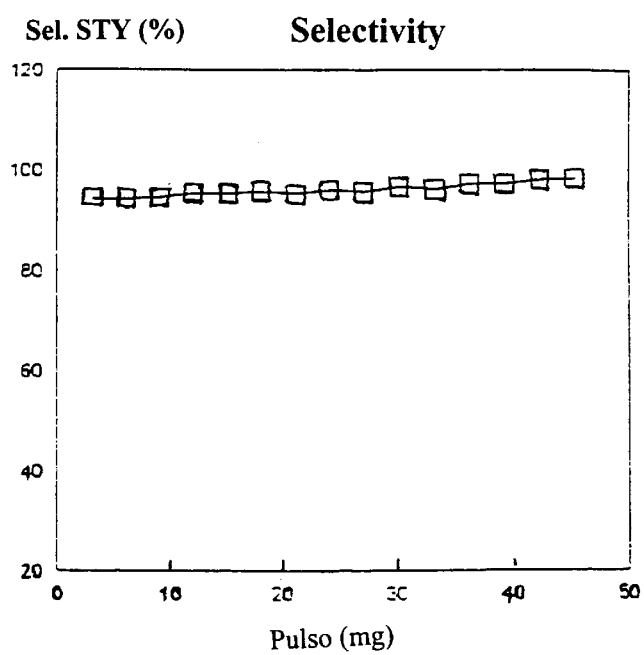

FIG. 3.2A
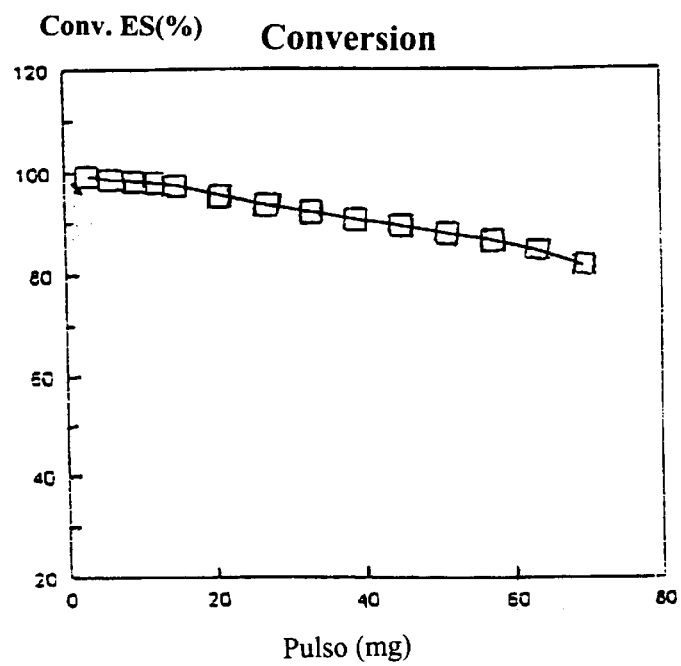
FIG. 3.2B
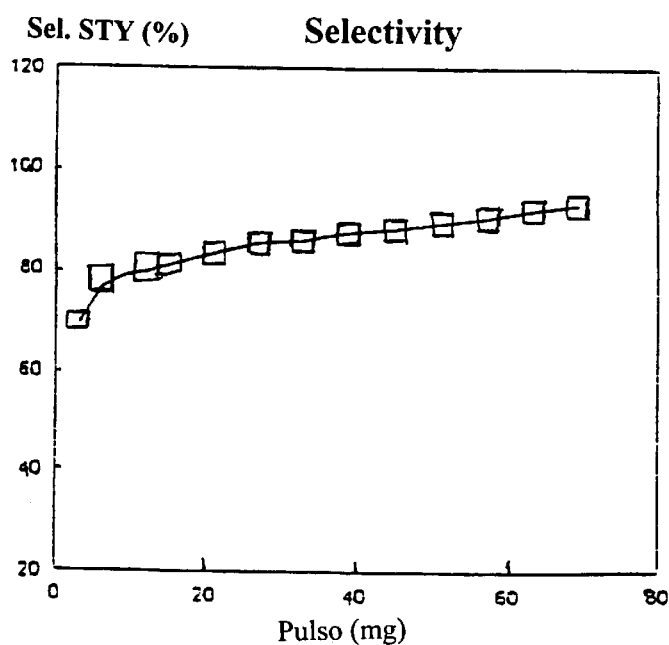

FIG. 3.3A
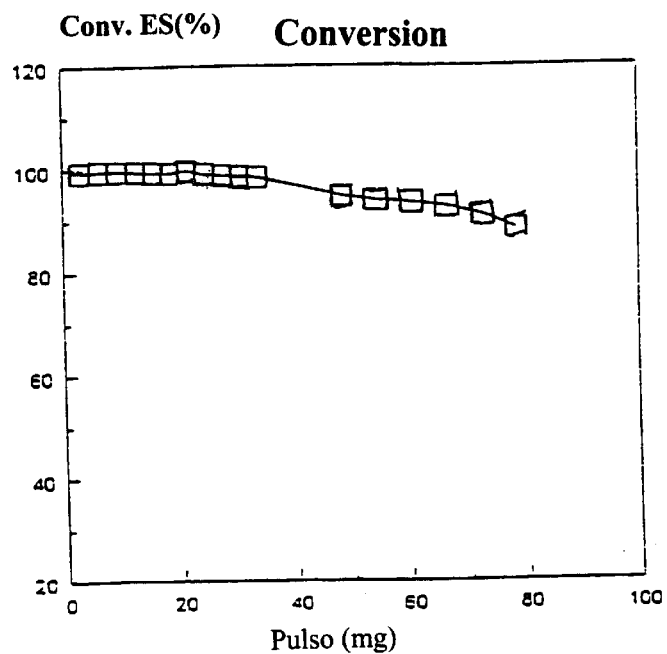
FIG. 3.3B
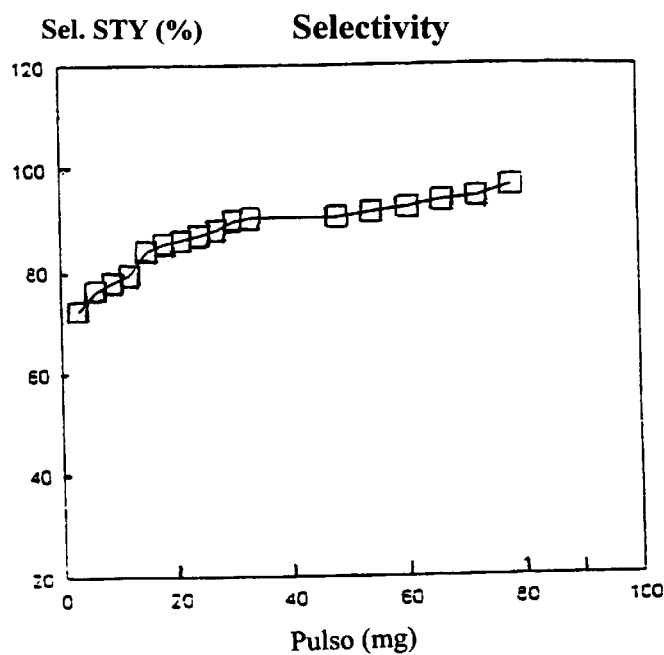

FIG. 3.4A
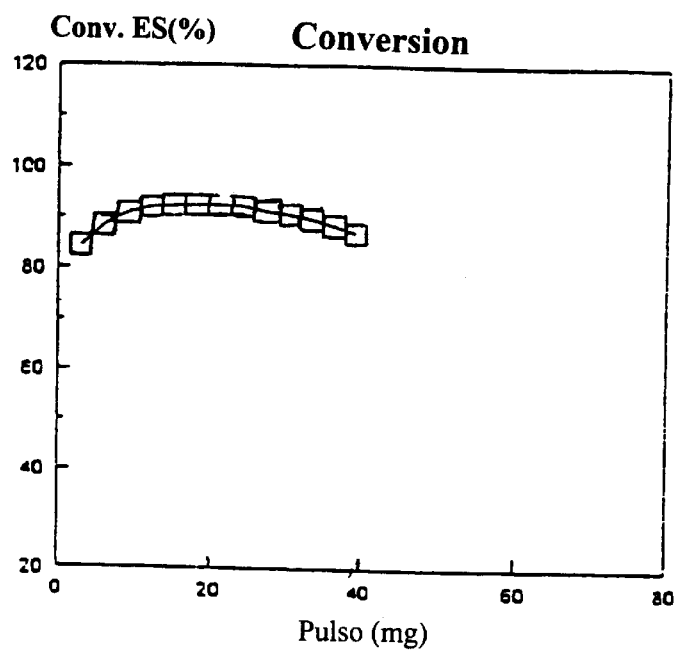
FIG. 3.4B
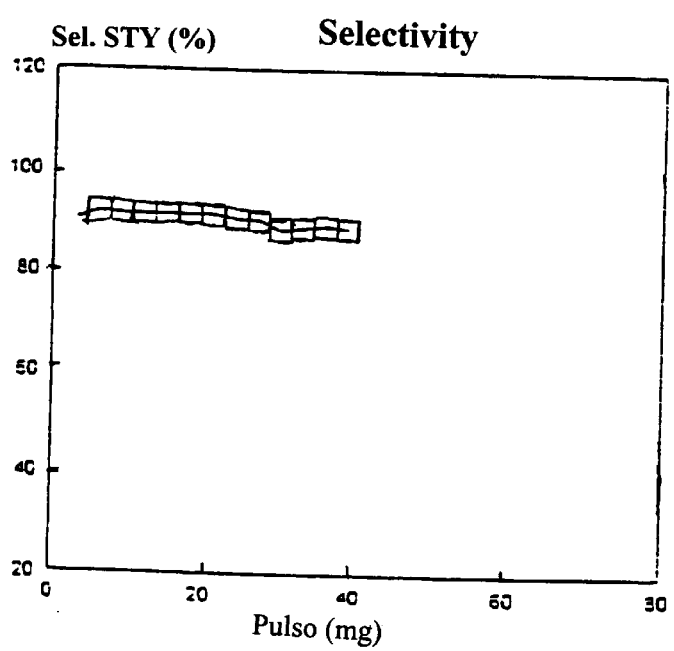

FIG. 3.5A
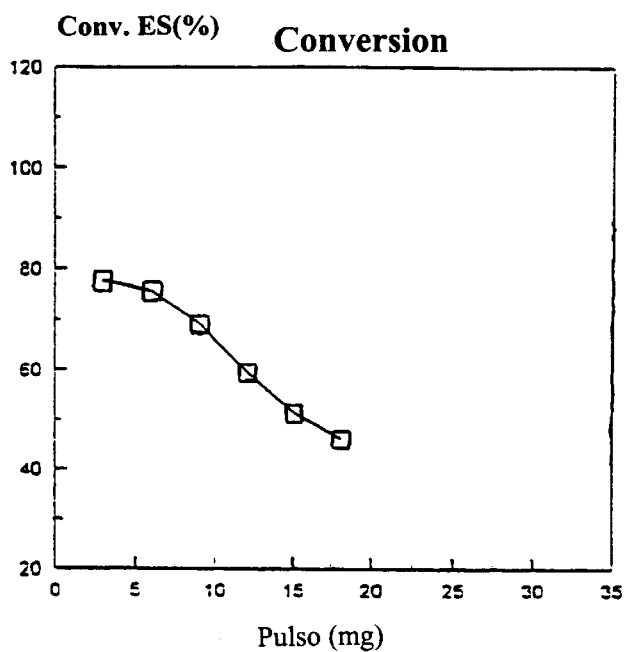
FIG. 3.5B
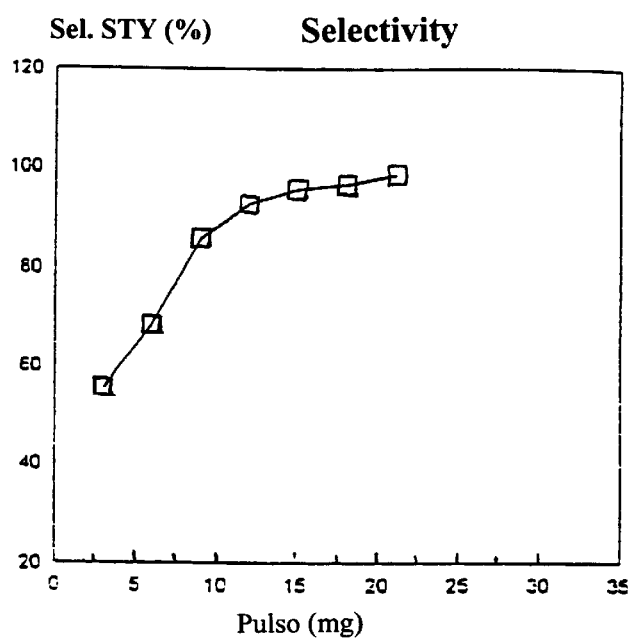

FIG. 3.6A
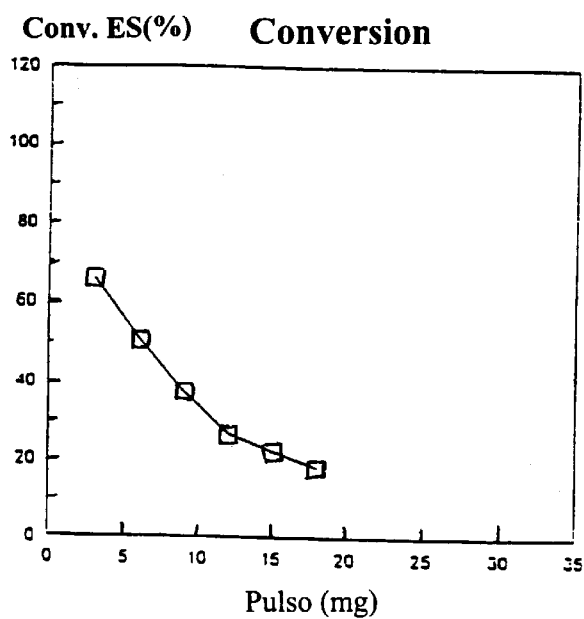
FIG. 3.6B
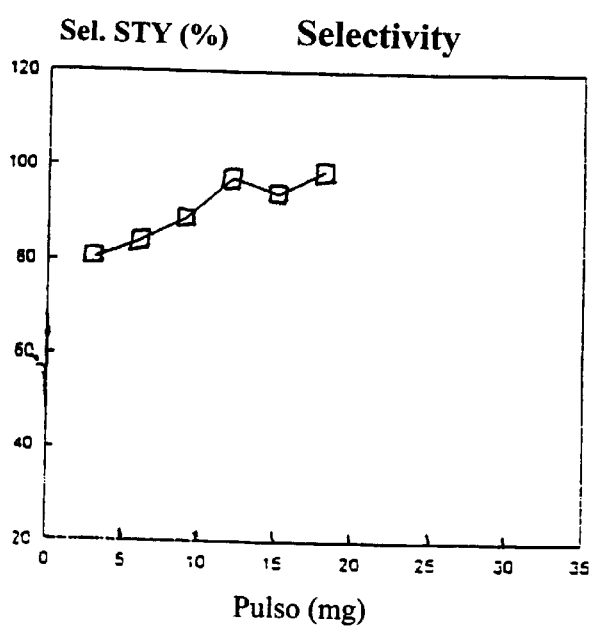

FIG. 3.7A
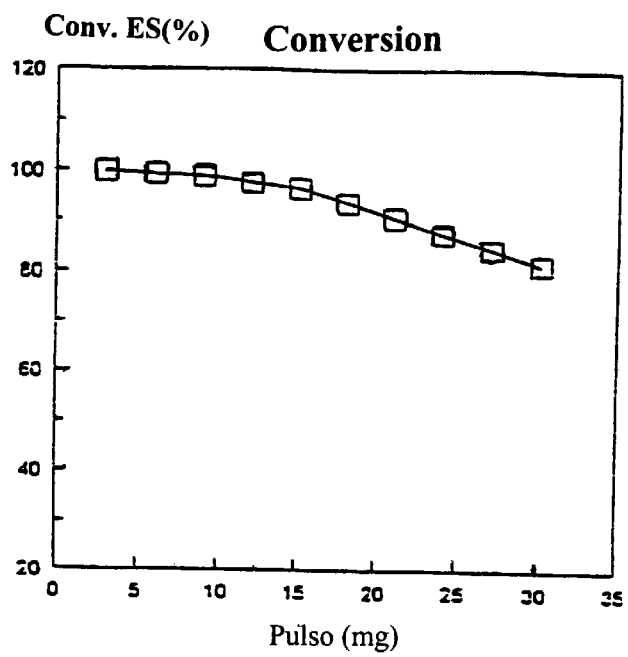
FIG. 3.7B
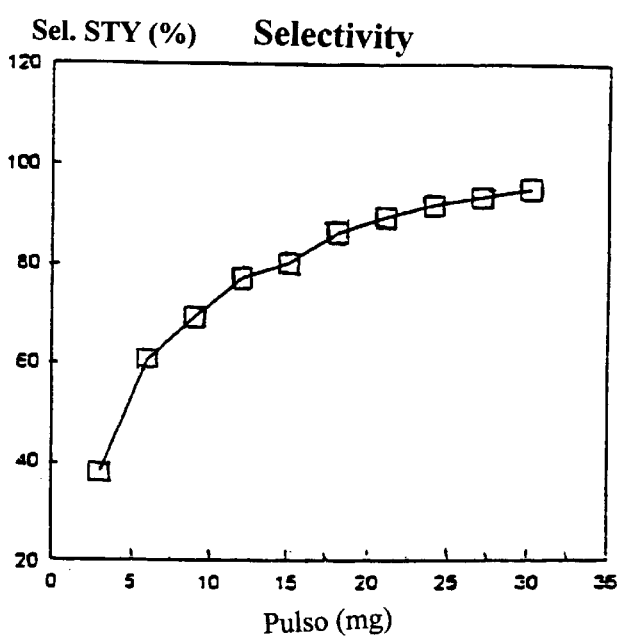

FIG. 3.8A
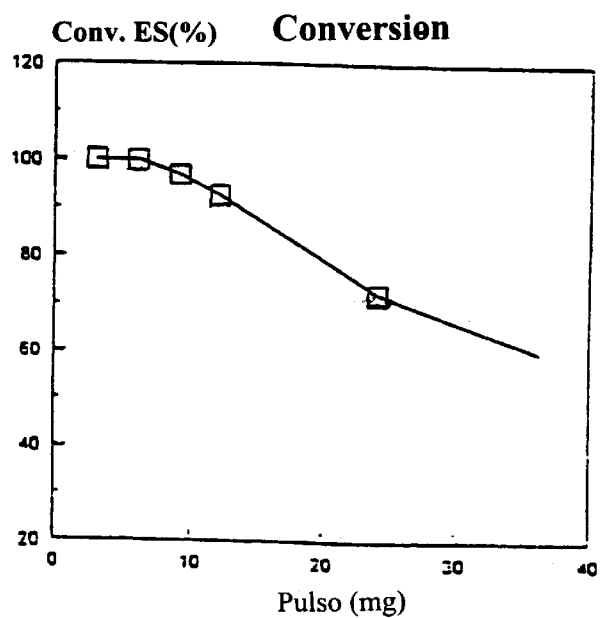
FIG. 3.8B
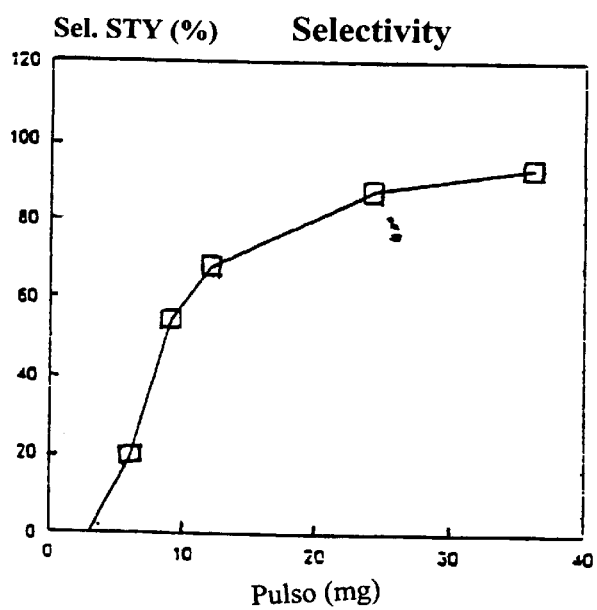

FIG. 3.9A
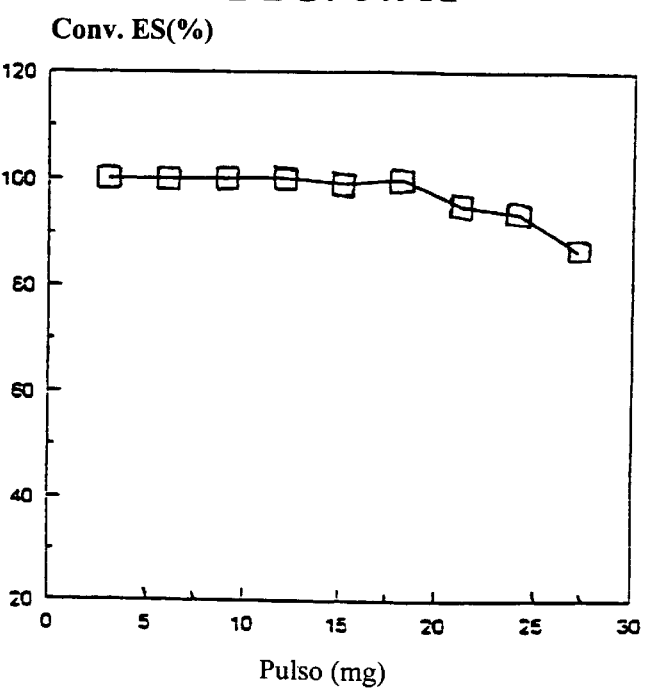
FIG. 3.9B
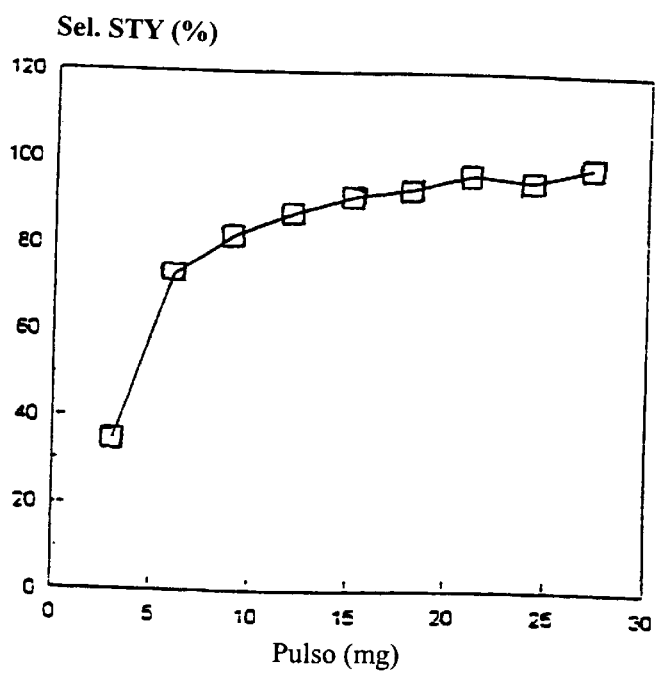

CATALYST SYSTEM FOR THE OXIDATIVE DEHYDROGENATION OF ALKYLAROMATICS OR PARAFFINS TO THE CORRESPONDING ALKENYLAROMATICS OR OLEFINS

BACKGROUND OF THE INVENTION

1. Field of the Invention

The present invention relates to a catalytic system and the relative process for the oxidative dehydrogenation of alkylaromatics, in particular ethylbenzene, or of paraffins to the corresponding alkenylaromatics, in particular styrene, or to the corresponding olefins.

2. Description of the Background

Styrene, which is an important intermediate for the production of plastic materials, is mainly used in the production of polystyrenes (GPPS crystals, shock-resistant HIPS and expandable EPS), acrylonitrile-styrene-butadiene (ABS) copolymers and styrene-acrylonitrile (SAN) copolymers of styrene-butadiene rubbers (SBR).

At present, styrene is mainly produced by means of two processes: by the dehydrogenation of ethylbenzene (EB) and, as coproduct, in the epoxidation of propylene with ethylbenzene hydroperoxide with catalysts based on molybdenum complexes.

An alternative method for the production of the monomer is the dehydrogenation of ethylbenzene with the contemporaneous oxidation of hydrogen which can be carried out in the presence of or without oxygen.

Oxidative dehydrogenation without oxygen consists in the use of one or more metal oxides which, apart from catalyzing the dehydrogenation reaction of ethylbenzene, are capable of oxidizing, by means of the oxygen available on the oxide itself, the hydrogen produced, in order to favor the equilibrium shift towards the formation of styrene (STY) by means of the reaction

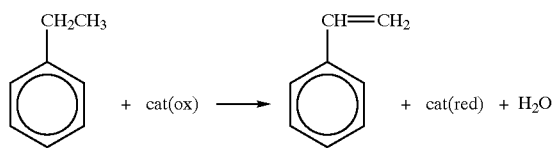

(1)

It is evident from the reaction (1) that the catalyst also participates in the stoichiometry of the reaction, by acting as reagent: at the beginning of the reaction it is in an oxidative state ($cat_{ox}$) capable of giving part of its oxygen and becoming a reduced species ($car_{red}$). In order to make the reaction catalytic it is necessary for the reduced catalyst to be able to easily recuperate the oxygen to be transformed into the starting oxidized species, useful for a new oxidative dehydrogenation cycle, by means of the reaction

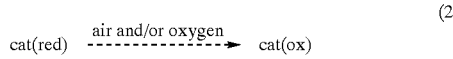

(2)

This particular way of conducting the dehydrogenation has the same advantages as the traditional oxidative dehydrogenation, i.e. In the presence of oxygen, allowing the heat necessary for the dehydrogenation to be produced and the equilibrium of the dehydrogenation reaction to be shifted towards the products, without disadvantages such as the by-production of oxygenated compounds deriving from the use of an oxidation gas.

The idea of carrying out the oxidative dehydrogenation of hydrocarbons without an oxidating gas was already made known in the first half of the 60s' by U.S. Pat. No. 3,118,007 of Bayer. This patent claims a process for the dehydrogenation of hydrocarbons without oxidating gases and with catalysts based on iron oxides which also act as oxygen transporters. It also describes the possibility of operating under fluid bed conditions to allow the continuous removal of the catalyst to be subjected to a reoxidation phase and subsequent recycling to the reaction phase.

Various patents on oxidative dehydrogenation without oxidating gases have been filed in the last few years, of which the most pertinent are the following.

EP-482276 of FINA describes a process by which a total conversion of ethylbenzene is already obtained at 505° C. with a catalyst which acts as oxygen transporter and which once exhausted, can be regenerated in a second reactor by treatment with air. The catalyst, containing oxides of transition metals, preferably based on vanadium supported on magnesium, has a high dehydrogenating activity as well as a strong tendency to provide structural oxygen for the combustion of the hydrogen. The results specified in this patent demonstrate that combustion is the most critical phase of the reaction: at the beginning of the catalytic activity, in fact, the styrene is produced with a low selectivity together with a high quantity or carbon oxides deriving from the combustion of ethylbenzene and/or styrene. The same patent shows that a partial pre-reduction of the catalyst, by treatment with carbon monoxide, enables its strong oxidating capacity to be moderated and high selectivities to be obtained already in the first phases of activity. In this case however, the conversion rapidly drops and soon becomes stabilized at values of approximately 50%.

GB-2297043 of BASF claims the use of a catalyst consisting of a mixed oxide based on bismuth, titanium, lanthanum, potassium and treated with a noble metal, for the oxidative dehydrogenation of ethylbenzene without oxygen. The results indicated do not allow the catalytic performances to be accurately evaluated over a period of time. In the text of the patent it is stated that the catalyst is initially very active but not very selective with the formation of compounds deriving from the combustion of hydrocarbons. As already observed in the case of the FINA patent, as the process proceeds the catalyst becomes less active and increasingly more selective until it reaches the maximum value.

SUMMARY OF THE INVENTION

We have surprisingly found that with the use of catalysts based on vanadium and bismuth suitably supported, with respect to the know catalysts described above, in addition to there being better selectivity characteristics, mainly at the beginning of the reaction, and a higher total productivity, the duration of the life of the catalyst itself is also greater.

The catalytic system of the present invention for the Om oxidative dehydrogenation of alkylaromatics (in particular ethylbenzene) or paraffins to the corresponding alkenylaromatics (in particular styrene) or to the corresponding olefins, consists of:

a vanadium oxide;

a bismuth oxide;

and a carrier based on magnesium, wherein
the vanadium, expressed as $V_2O_5$, is in a quantity ranging from 1 to 15% by weight, preferably from 2 to 10%,
the bismuth, expressed as $Bi_2O_3$, ranges from 2 to 30% by weight, preferably from 5 to 25% by weight, the complement to 100 being the carrier.

BRIEF DESCRIPTION OF THE DRAWINGS

FIGS. 3.1a and 3.1b respectively show the conversion of ethylbenzene and selectivity to styrene in oxidative dehydrogenation employing the catalyst of Example 1;

FIGS. 3.2a and 3.2b respectively show the conversion of ethylbenzene and selectivity to styrene in oxidative dehydrogenation employing the catalyst of Example 2;

FIGS. 3.3a and 3.3b respectively show the conversion of ethylbenzene and selectivity to styrene in oxidative dehydrogenation employing the catalyst of Example 3;

FIGS. 3.4a and 3.4b respectively show the conversion of ethylbenzene and selectivity to styrene in oxidative dehydrogenation employing the catalyst of Example 4;

FIGS. 3.5a and 3.5b respectively show the conversion of ethylbenzene and selectivity to styrene in oxidative dehydrogenation employing the catalyst of Example 5;

FIGS. 3.6a and 3.6b respectively show the conversion of ethylbenzene and selectivity to styrene in oxidative dehydrogenation employing the catalyst of Example 6;

FIGS. 3.7a and 3.7b respectively show the conversion of ethylbenzene and selectivity to styrene in oxidative dehydrogenation employing the catalyst of Example 7;

FIGS. 3.8a and 3.8b respectively show the conversion of ethylbenzene and selectivity to styrene in oxidative dehydrogenation employing the catalyst of Example 8; and FIGS. 3.9a and 3.9b respectively show the conversion of ethylbenzene and selectivity to styrene in oxidative dehydrogenation employing the catalyst of Example 9.

The carrier based on magnesium is preferably selected from:
carriers consisting of magnesium oxide;
carriers consisting of magnesium oxide and zirconium oxide, in which the magnesium, expressed as MgO, preferably ranges from 20 to 40% by weight with respect to the catalytic system, the zirconium, expressed as $ZrO_2$, ranges from 30 to 50% by weight with respect to the catalytic system;
carriers consisting of magnesium and aluminum hydrotalcites, in which the atomic ratio magnesium/aluminum preferably ranges from 70/30 to 30/70.

The process for preparing the catalytic system described above can be essentially effected by means of the following steps:
preparation of solutions or suspensions based on derivatives of the components of the catalytic system;
mixing of the solutions or suspensions prepared, until gelation of the mixture;
drying oL the gel obtained;
calcination of the dried solid at a temperature ranging from 550 to 780° C.

The catalytic system claimed can be applied to any fixed, fluid or mobile-bed dehydrogenation technology of ethylbenzene.

Figure 1:
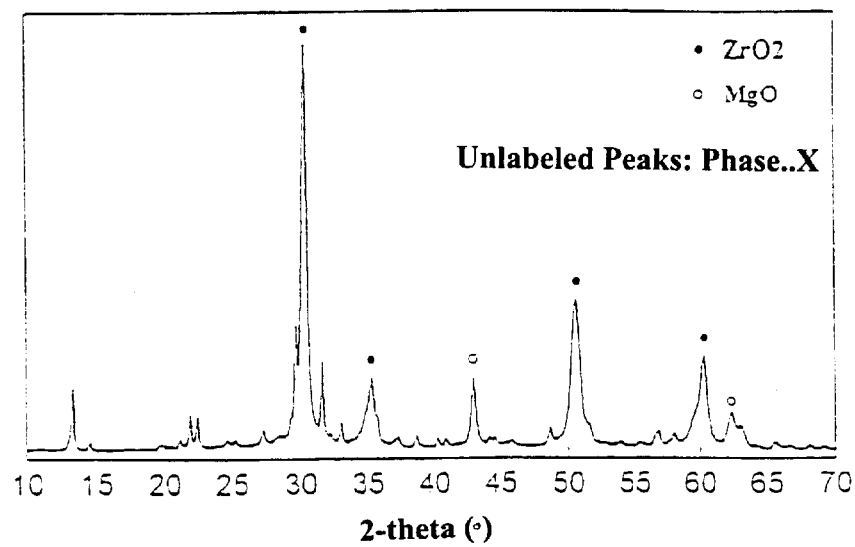
FIG. 1 is an X-ray diffraction spectrum of vanadium oxide or bismuth oxide supported on a carrier of magnesium oxide and zirconium oxide.

When the catalytic system consists of vanadium oxide or bismuth oxide on a carrier consisting of magnesium oxide and zirconium oxide, in its calcined form at 750° C. (see example 1), it has an X-ray diffraction spectrum, registered by means of a vertical goniometer equipped with an electronic impulse counter system and using CuKα radiation ($\lambda$=1.54178 Å), containing the main reflections shown in table 1 (where d indicates the interplanar distance) and in FIG. 1.

We can see the presence of an unknown phase (not structurally characterized) indicated as Phase (X), as well as the $ZrO_2$ and MgO phases.

We have also found that again in the case of a catalytic system consisting of vanadium oxide, bismuth oxide on a carrier consisting of magnesium oxide and zirconium oxide, when the last part of the preparation, i.e. the calcination, is carried out within a very specific temperature range, a catalytic system is obtained, which surprisingly has a better catalytic activity with respect to the catalytic system described above, calcined at higher temoeratures.

Figure 2:
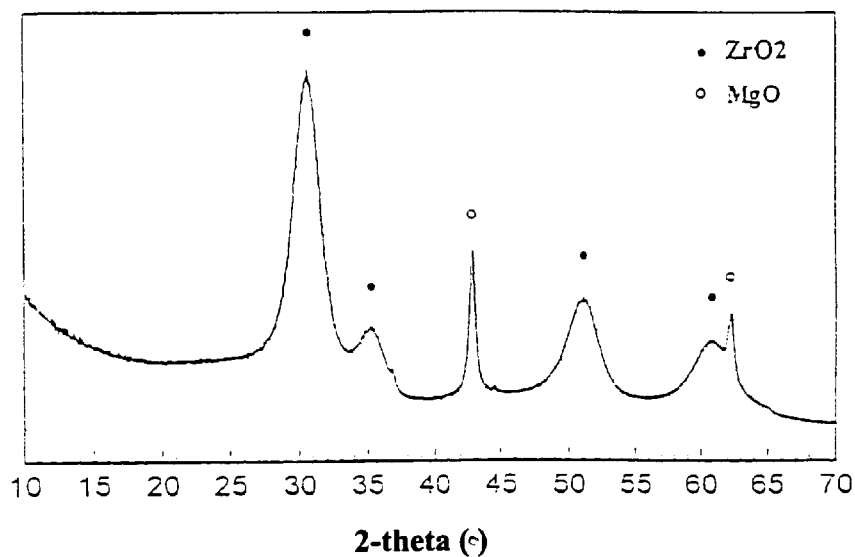
FIG. 2 is an X-ray diffraction spectrum of vanadium oxide and bismuth oxide supported on a carrier of magnesium oxide and zirconium oxide.

This catalytic system with an improved catalytic activity, which forms a further object of the present invention, consists of:
a vanadium oxide;
a bismuth oxide;
and a carrier consisting of magnesium oxide and zirconium oxide,
wherein the vanadium, expressed as $V_2O_5$, is in a quantity ranging from 1 to 15% by weight, preferably from 2 to 10%, more preferably from 2 to 5%,
the bismuth, expressed as $Bi_2O_3$, ranges from 2 to 30% by weight, preferably from 5 to 25% by weight,
the magnesium, expressed as MgO, ranges from 20 to 40% by weight,
the zirconium, expressed as $ZrO_2$, ranges from 30 to 50% by weight and is characterized in that it has, in its calcined form, an X-ray diffraction spectrum, registered by means of a vertical goniometer equipped with an electronic impulse counter system and using CuKα radiation ($\lambda$=1.54178 Å), containing the main reflections shown in table 2 (where d indicates the interplanar distance) and in FIG. 2.

With respect to the catalytic system described above, calcined at 750° C., it can be seen that this system does not have the diffraction peaks attributed to Phase (X).

As mentioned above, the preparation process of this catalytic system is analogous to that described above where the calcination, which forms the last step of the preparation, is effected at a temperature ranging from 585 to 615° C.

The, process for preparing the catalytic system described above, therefore essentially comprises the following steps:
preparation of solutions or suspensions based on derivatives of the components of the catalytic system;
mixing of the solutions or suspensions prepared, until gelation of the mixture;
drying of the gel obtained;
calcination of the dried solid at a temperature ranging from 585 to 615° C.

The process, a further object of the present invention for the oxidative dehydrogenation of alkylaromatics, in particular ethylbenzene, or paraffins into the corresponding alkenylaromatics, in particular styrene, or into the corresponding olefins, substantially consists in reacting the alkylaromatic or paraffin, in a reactor, operating at a temperature ranging from 400 to 750° C., at a pressure ranging from 0.1 to 30 psia and with a GHSV space velocity ranging from 0.01 to 10 sec$^{-1}$, preferably from 0.1 to 1 sec$^{-1}$, (normal-litres of hydrocarbon/sec per liter of catalyst), optionally in the presence of a diluent, with the catalytic system described above and in regenerating this catalytic system in a regenerator, by burning the coke deposited during the reaction phase, operating at a temperature of over 400° C.

The oxidating medium used in this process can be oxygen and/or air.

The possible diluent can be for example $N_2$, $CH_4$, $H_2O_{vapour}$, CO, $CO_2$, etc.

Some examples are provided for a better illustration of the present invention which should not be considered however as limiting the scope of the invention.

EXAMPLES 9 syntheses of catalysts are described (of which 5 comparative) followed by the corresponding catalytic tests.

Example 1
Synthesis of Catalyst Supported on MgO and $ZrO_2$
The following mixtures are prepared:
suspension A: 4.30 g of $VOSO_4 5H_2O$ in 20 g of ethanol (M.W.=253 gmol$^{-1}$, 0.0085 mol $V_2O_5$)
solution B: 59.46 g of $Zr(OC_3H_7)_4$ at 70% (M.W.=327 gmol$^{-1}$, 0.127 mol $ZrO_2$)
solution D: 3.79 g of TPA-OH (40%) in 12 g of $H_2O$ (M.W.=203 gmol$^{-1}$, 0.0075 mol).
Solution B is added to suspension A under heat (about 60° C.) and under magnetic stirring; a brown suspension (suspension C) is obtained. 8.24 g of $Bi(NO_3)_3 5H_2O$ (M.W.=485 gmol$^{-1}$, 0.0085 mol $Bi_2O_3$) and 11.65 g of MgO (M.W.=40.3 gmol$^{-1}$, 0.29 mol MgO) are added under heat and under magnetic stirring to the suspension thus obtained; a suspension is obtained to which solution D is added. The addition of the alkylammonium hydroxide causes the formation of a gel which is left to age for 24 hours; the gel is subsequently dried at 120° C. overnight and finally calcined at 750° C. for 4 hours in a stream of air.

Example 2
Synthesis of Catalyst Supported on Mg—Al Hydrotalcite
0.97 g of $NH_4VO_3$ (M.W.=117 gmol$^{-1}$, 0.0041 mol $V_2O_5$) are dissolved in 40 g of water; 7.28 g of hydrotalcite ($MgO/Al_2O_3$=1 by weight) are added to the solution thus obtained. 3.98 g of $Bi(NO_3)_3 5H_2O$ (M.W.=485 gmol$^{-1}$, 0.0041 mol $Bi_2O_3$) are added to the yellow-white suspension thus obtained. The yellow-orange suspension is maintained under stirring for 5 hours and then dried and the solid calcined at 650° C. for 4 hours in air.

Example 3
Synthesis of Catalyst Supported on MgO
2.80 g of $NH_4VO_3$ (M.W.=117 gmol$^{-1}$, 0.012 mol $V_2O_5$) are dispersed in 100 g of water at a temperature of 90° C. This suspension is added to the suspension obtained by adding, under heat, at a temperature of 90° C., 15.00 g of MgO (M.W.=40.3 gmol$^{-1}$, 0.375 mol MgO) and 11.64 g of $Bi(NO_3)_3 5H_2O$ (M.W.=485 gmol$^{-1}$, 0.012 mol $Bi_2O_3$) to 100 g of water. The mixture thus obtained is left to digest at 90° C. for 2 hours and is then dried under a stream of $N_2$. It is subsequently calcined in a stream of air for 4 hours at a temperature of 600° C.

Example 4
Synthesis of Catalyst Supported on MgO and $ZrO_2$ Calcined at 600° C.
A catalyst is prepared, consisting of $V_2O_5$ and $Bi_2O_3$ supported on MgO and $ZrO_2$ prepared analogously to example 1 except for the calcination which is carried out for 4 hours in a stream of air, at 600° C. instead of 750° C.

Example 5
Comparative: Vanadium Oxide Supported on MgO and $ZrO_2$
The following mixtures are prepared:
suspension A: 2.15 g of $VOSO_4 5H_2O$ in 20 g of ethanol (M.W.=253 gmol$^{-1}$, 0.0042 mol $V_2O_5$)
solution B: 59.46 g of $Zr(OC_3H_7)_4$ at 70% (M.W.=327 gmol$^{-1}$, 0.127 mol $ZrO_2$)
solution D: 3.79 g of TPA-OH (40%) in 12 g of $H_2O$ (M.W.=203 gmol$^{-1}$, 0.0075 mol).
Solution B is added to suspension A under heat (about 60° C.) and under magnetic stirring; a brown suspension (suspension C) is obtained. 11.65 g of MgO (M.W.=40.3 gmol$^{-1}$, 0.29 mol MgO) are added under heat and under magnetic stirring to the suspension thus obtained; a suspension is obtained to which solution D is added. The addition of the alkylammonium hydroxide causes the formation of a gel which is left to age for 24 hours; the gel is subsequently dried at 120° C. overnight and finally calcined at 750° C. for 4 hours in a stream of air.

Example 6
Comparative: Bismuth Oxide Supported on MgO and $ZrO_2$
The following solutions are prepared:
solution A: 59.46 g of $Zr(OC_3H_7)_4$ at 70% (M.W.=327 gmol$^{-1}$, 0.127 mol $ZrO_2$)
solution C: 3.79 g of TPA-OH (40%) in 12 g of $H_2O$ (MW.=203 gmol$^{-1}$, 0.0075 mol).
50 g of ethanol are added to solution A and 4.12 g of $Bi(NO_3)_3 5H_2O$ (M.W.=485 gmol$^{-1}$, 0.0042 mol $Bi_2O_3$) and 11.65 g of MgO (M.W.=40.3 gmol$^{-1}$, 0.29 mol MgO) are added under magnetic stirring; a suspension is obtained, to which solution C is added. The addition of the alkylammonium hydroxide causes the formation of a gel which is left to age for 24 hours; the gel is subsequently dried at 120° C. overnight and finally calcined at 750° C. for 4 hours in a stream of air.

Example 7
Comparative: Vanadium Oxide Supported on Hydrotalcite
1.93 g of $NH_4VO_3$ (M.W.=117 gmol$^{-1}$, 0.0082 mol $V_2O_5$) are dissolved under heat in 40 g of water; the solution thus obtained is used to impregnate 8.50 g of hydrotalcite (MgO/$Al_2O_3$=1 by weight). After impregnation the cake is dried in an oven at 80° C. overnight and subsequently calcined at 650° C. for 4 hours in air.

Example 8
Comparative: Vanadium Oxide-Alumina-Magnesia
The following mixtures are prepared:
solution A: 1.82 g of $NH_4VO_3$ (M.W.=117 gmol$^{-1}$, 0.0156 mol V) are dissolved in 20 g of water alkalinized by 7.90 g of TPA-OH (40% in water) (M.W.=203 gmol$^{-1}$, 0.0156 mol)
solution B: 20.54 g of $Al(sec-OC_4H_9)_3$ (M.W.=246 gmol$^{-1}$, 0.0835 mol Al) in 50 g of ethanol.
Solution A is added to suspension B; 4.25 g of MgO (M.W.=40.3 gmol$^{-1}$, 0.105 mol MgO) are added under magnetic stirring to suspension C thus obtained. The suspension is maintained under stirring for 5 hours, is then dried and the solid is calcined at 650° C. for 4 hours in air.

Example 9

Comparative—Vanadium-Magnesia

Catalyst prepared according to example 1 of EP-0403462 (FINA).

The following mixtures are prepared:

solution A: 5.6 g of $NH_4VO_3$ are dissolved under heat in 100 ml of $H_2O$ suspension B: 15.00 g of MgO are suspended In 100 g of $H_2O$.

The suspension is then heated to a temperature of 90° C.

Solution A is added under heat to suspension B and the resulting suspension is left under magnetic stirring for 2 h. It is then heated to 120° C. and the solvent is eliminated in a stream of $N_2$.

The dried product is calcined at 600° C. for 4 h.

Catalytic Tests of the Catalysts of Examples 1–9

All the catalytic tests were carried out in a micro-reactor with pulse feeding of ethylbenzene. In all the tests about 500 mg of catalyst were charged, which were activated in an atmosphere of air at 500° C. for 2 hours. At the end of this pretreatment, the reactions were carried out at 500° C. (except for the one using the catalyst of example 4 effected at 480° C.), feeding pulses of about 3 mg of ethylbenzene, with a contact time of about 1.1 sec.

The conversions of ethylbenzene and selectivities to styrene are indicated in the graphs of FIGS. 3.1a–3.9a and 3.1b–3.9b respectively (wherein the number following 3 refers to the synthesis example of the catalyst used).

TABLE 1

| 2θ(CuKα) | $d_{hkl}$ (Å) | $ZrO_2$ | MgO | X phase |
|---|---|---|---|---|
| 9.67 | 9.141 | | | X |
| 13.35 | 6.628 | | | X |
| 14.53 | 6.092 | | | X |
| 19.76 | 4.491 | | | X |
| 21.14 | 4.198 | | | X |
| 21.92 | 4.051 | | | X |
| 22.48 | 3.951 | | | X |
| 24.66 | 3.607 | | | X |
| 25.19 | 3.533 | | | X |
| 27.26 | 3.269 | | | X |
| 29.69 | 3.006 | | | X |
| 30.33 | 2.945 | X | | |
| 31.58 | 2.831 | | | X |
| 32.97 | 2.715 | | | X |
| 35.23 | 2.545 | X | | |
| 37.20 | 2.415 | | X | |
| 38.62 | 2.329 | | | X |
| 40.25 | 2.239 | | | X |
| 40.87 | 2.206 | | | X |
| 42.98 | 2.103 | | | |
| 44.17 | 2.049 | | | X |
| 44.57 | 2.031 | | | X |
| 45.83 | 1.978 | | | X |
| 48.66 | 1.870 | | | X |
| 50.56 | 1.804 | X | | |
| 56.76 | 1.621 | | | X |
| 57.98 | 1.589 | | | X |
| 60.26 | 1.535 | X | | |
| 62.36 | 1.488 | | X | |
| 63.10 | 1.472 | X | | |

TABLE 2

| 2θ(CuKα) | $d_{hkl}$ (Å) | $ZrO_2$ | MgO |
|---|---|---|---|
| 30.54 | 2.925 | X | |
| 35.19 | 2.548 | X | |
| 36.82 | 2.439 | | X |

TABLE 2-continued

| 2θ(CuKα) | $d_{hkl}$ (Å) | $ZrO_2$ | MgO |
|---|---|---|---|
| 42.86 | 2.108 | | X |
| 51.01 | 1.789 | X | |
| 60.70 | 1.524 | X | X |
| 62.23 | 1.491 | | |

What is claimed is:

1. A catalyst system consisting of from 1 to 15% by wt of $V_2O_5$, and from 2 to 30% by wt of $Bi_2O_3$ in combination functioning as catalytically active oxides for the oxidative dehydrogenation of alkylaromatics and paraffins, the percentages based on the weight of the catalyst system, supported on a carrier which is the remainder of the catalyst system and is a member selected from the group consisting of (i) magnesium oxide, (ii) a combination of magnesium oxide and zirconium oxide and (iii) a combination of magnesium hydrotalcite and aluminum hydrotalcite.

2. The catalyst system according to claim 1, wherein the carrier embodiment (ii) consists of 20 to 40% by wt of magnesium oxide and 30 to 50% by wt of zirconium oxide, based on the weight of the catalyst system.

3. The catalyst system according to claim 2, wherein the catalyst system has the X-ray diffraction spectrum indicated in Table 2.

4. The catalyst system according to claim 3, wherein the amount of said vanadium component expressed as $V_2O_3$ ranges from 2 to 10% by wt and the amount of said bismuth component expressed as $Bi_2O_3$ ranges from 5 to 25% by wt.

5. The catalyst system according to claim 4, wherein the amount of said vanadium component expressed as $V_2O_3$ ranges from 2 to 5% by wt.

6. A method of preparing the catalyst system according to claim 3, which comprises:

preparing solutions or suspensions of vanadium and bismuth derivatives of the vanadium oxide and bismuth oxide catalyst components and metal components of said carrier;

mixing the prepared solutions or suspensions of catalyst materials until the mixture gels;

drying the gel obtained; and calcining the dried gel at a temperature ranging from 585 to 615° C.

7. The catalyst system according to claim 1, wherein the atomic ratio of magnesium/aluminum in the hydrotalcites of carrier embodiment (ii) ranges from 70/30 to 30/70.

8. The catalyst system according to claim 1, wherein the amount of said vanadium component expressed as $V_2O_5$ ranges from 2 to 10% by wt and the amount of said bismuth component expressed as $Bi_2O_3$, ranges from 5 to 25% by wt.

9. A catalyst system consisting of from 1 to 15% by wt of $V_2O_5$, and from 2 to 30% by wt of $Bi_2O_3$ in combination functioning as catalytically active oxides for the oxidative dehydrogenation of alkylaromatics and paraffins, the percentages based on the weight of the catalyst system, supported on a carrier which consists of a combination of magnesium oxide and zirconium oxide in which the magnesium oxide content ranges from 20 to 40% by wt, based on the weight of the catalyst system.

* * * * *